United States Patent [19]

McShane

[11] Patent Number: 4,704,156

[45] Date of Patent: Nov. 3, 1987

[54] METHOD FOR PLANT GROWTH REGULATION

[75] Inventor: Lawrence J. McShane, Whiteland, Ind.

[73] Assignee: Eli Lilly and Company, Indianapolis, Ind.

[21] Appl. No.: 860,561

[22] Filed: May 7, 1986

[51] Int. Cl.$^4$ .................... C07C 69/74; A01N 53/00
[52] U.S. Cl. .......................................... 71/88; 71/106;
71/113; 71/118; 260/500.5 H; 544/176;
560/124; 562/506; 564/148; 564/149; 564/151;
564/152; 564/155; 564/190
[58] Field of Search ................... 560/124; 544/176;
564/148, 190, 155, 152, 149, 151; 71/88, 106,
118, 113; 260/500.5 H

[56] References Cited

U.S. PATENT DOCUMENTS

| | | | |
|---|---|---|---|
| 3,246,975 | 3/1962 | Hopkins | 71/3.5 |
| 3,277,107 | 10/1966 | Neighbors | 260/396.8 |
| 3,277,171 | 10/1966 | Hopkins | 260/557 |
| 3,306,727 | 2/1967 | Neighbors | 71/2.6 |
| 3,320,121 | 5/1967 | Douros | 167/30 |
| 3,328,156 | 6/1967 | Hopkins | 71/2.6 |
| 3,462,453 | 8/1969 | Pennsalt | 260/333.5 |
| 3,701,799 | 10/1972 | Foncher | 260/468 |
| 3,720,703 | 3/1973 | Elliott | 560/124 |
| 3,773,824 | 11/1973 | Storenz | 260/484 |
| 3,846,112 | 11/1974 | Foncher | 71/76 |
| 3,853,952 | 12/1974 | Kishida | 260/469 |
| 3,856,976 | 12/1974 | Hunter | 560/124 |
| 3,917,667 | 11/1975 | Verbrugge | 560/124 |
| 3,927,068 | 12/1975 | Searle | 560/124 |
| 4,220,591 | 9/1980 | Holan | 260/340.5 |
| 4,418,202 | 11/1983 | Fayter | 549/496 |

FOREIGN PATENT DOCUMENTS

67/1181 7/1967 South Africa.
67/1349 7/1967 South Africa.

OTHER PUBLICATIONS

Preparation of 1,2,2-trichlorocyclopropane Carboxylic Acid: D'yakoaov et al., *J. Org. Chem. USSR* 3, 256 (1976).

Baird, Tetrahedron Letters, 26, pp. 6353-6356.

*Primary Examiner*—Michael L. Shippen

[57] ABSTRACT

1,2,2-Trihalocyclopropane 1-carboxylic acids and derivatives thereof are useful in regulating the growth and flowering of plants when applied as a foliar spray or as a post emergent or pre-emergent soil treatment.

23 Claims, No Drawings

METHOD FOR PLANT GROWTH REGULATION

BACKGROUND OF THE INVENTION

This invention relates to methods for regulating plant growth and for enhancing plant flowering and fruiting by application of certain trihalo substituted cyclopropane compounds. More particularly, it relates to the regulation of plant growth utilizing 1,2,2-trihalo substituted cyclopropane 1-carboxylic acid compounds and derivatives thereof.

A wide variety of substituted cyclopropane-type compounds are known in the art. European Pat. No. 136,615A, describes certain 1-methylaminocyclopropane 1-carboxylic acid derivatives taught to be useful as plant growth regulators. Popoff, et al., in U.S. Pat. No. 3,462,453, disclose certain dichlorocyclopropyl carboxylic acids which, among other disclosed compounds, are described collectively as useful for agricultural chemicals, lubricants, oil additives and pharmaceuticals; 2,2-dichlorocyclopropane-1-carboxylic acid is described as particularly useful as a flame retardant. Fayter, et al., in U.S. Pat. No. 4,418,202, describe certain 2-vinyl(or 2-ethyl)-1-cyano(aryl)cyclopropane-1-carboxylates which are said to be useful as plant growth regulators. The preparation of 1,2,2-trichlorocyclopropane carboxylic acid has been reported by D'yakoaov, et al., in *J. Org. Chem. USSR*, 3, 256 (1967).

That certain trihalosubstituted cyclopropane compounds can be utilized to regulate the growth of various plant species is heretofore known. An object of the present invention, therefore, is to provide a novel method of plant growth regulation employing certain trihalosubstituted cyclopropanes and related compounds.

SUMMARY OF THE INVENTION

This invention provides methods for regulating plant growth and for enhancing the flowering of plants comprising applying to a plant, to plant seeds, or to the soil locus of a growing plant an effective amount of a trihalocyclopropane compound of the formula

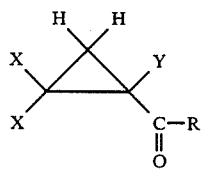

wherein:
X is simultaneously chloro or bromo;
Y is chloro or bromo;
R represents hydroxy, $C_1$–$C_4$ alkoxy, benzyloxy, nitrobenzyloxy, chlorobenzyloxy, benzhydryloxy or a group of the formula —$NR_1R_2$ wherein $R_1$ is hydrogen, $C_1$–$C_4$ alkyl or phenyl, and
$R_2$ is hydroxy, $C_1$–$C_4$ alkyl, $C_1$–$C_4$ alkanoyl, benzoyl, or a group of the formula —$NHR_3$ wherein $R_3$ is hydrogen, $C_1$–$C_4$ alkyl, phenyl, $C_1$–$C_4$ alkanoyl, or benzoyl;
or $R_1$ and $R_2$, together with the nitrogen atom to which they are attached, form a morpholino group; with the limitation that when $R_1$ is hydrogen, $R_2$ is hydroxy, $C_1$–$C_4$ alkyl, $C_1$–$C_4$ alkanoyl, benzoyl, or a group of the formula —$NHR_3$ wherein $R_3$ is hydrogen, $C_1$–$C_4$ alkyl, phenyl, $C_1$–$C_4$ alkanoyl or benzoyl; and
subject to the further limitation that when $R_1$ is $C_1$–$C_4$ alkyl or phenyl, $R_2$ is $C_1$–$C_4$ alkyl.

In a preferred aspect of this invention plant growth regulation is effected in plants by applying a compound defined by the above formula wherein one or more of the following characteristics apply:
(a) X is chloro;
(b) Y is chloro;
(c) R is hydroxy, 4-nitrobenzyloxy or group of the formula —$NR_1R_2$ wherein $R_1$ is hydrogen and $R_2$ is $C_1$–$C_4$ alkyl or —$NH_2$.

The compounds utilized in the method are synthesized by adaptation of literature procedures, such as that described by D'yakoaov, et al., in *J. Org. Chem. USSR*, 3, 256 (1967). Compounds useful as starting materials for synthesis of the present trihalocyclopropane compounds are either commercially available or they can be prepared according to art-recognized procedures.

A preferred method for synthesizing 1,2,2-trichlorocyclopropane compounds utilized in this invention is illustrated by the following general reaction scheme:

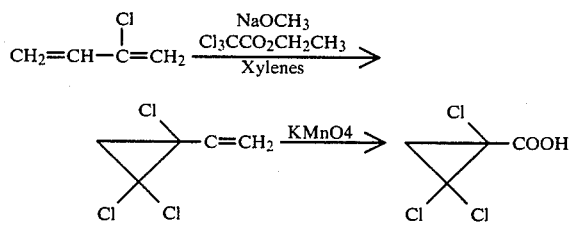

A conjugated, halo-diolefin is reacted with a dihalocarbene such as dichlorocarbene in an inert organic solvent such as benzene, toluene, xylene, or the like. Dichlorocarbene is generated in situ by the reaction of ethyl trichloroacetate or chloroform and sodium methoxide. The reaction is typically carried out at a temperature of about −10° to about −5° C. Normally the reaction is substantially complete after about 4 hours; however longer reaction times can be employed if desired.

Halo-substitution on the product 2-vinylcyclopropane compounds is governed by the nature of the halo-diolefin and the reactive dihalocarbene. For example the same reaction with dibromocarbene yields 1,1-dibromo-2-chloro-2-vinylcyclopropane. Some dibromovinylcyclopropanes are known in the art to be less stable intermediates than the corresponding dichlorovinylcyclopropane compounds.

The intermediate 1,1,2-trihalo-2-vinylcyclopropanes can be isolated and further purified if desired by routine methods, such as distillation or chromatography, or the intermediate compound can be oxidized in situ directly to 1,2,2-trihalocyclopropane carboxylic acid in aqueous potassium permanganate. This later procedure is preferred where the trihalovinylcyclopropane compound exhibits some degree of instability.

The carboxylic acid derivatives, i.e. the esters, amides, hydroxamides, hydrazides, etc., described in accordance with this invention are prepared from the corresponding carboxylic acids, typically via the corresponding reactive acid chloride intermediates.

DETAILED DESCRIPTION OF INVENTION

The following examples illustrate the preparation of representative compounds employed in the method of plant growth regulation provided by this invention.

EXAMPLE 1

1,2,2-TRICHLOROCYCLOPROPANE CARBOXYLIC ACID

Sodium methoxide (35 grams) was added to 200 ml of xylenes at room temperature and cooled to −10° C. A 50/50 mixture of chloroprene (96 grams) and xylenes was added dropwise to the sodium methoxide/xylenes mixture over a 20 minute addition period. The mixture was stirred rapidly during the addition period. The ethyl ester of trichloroacetic acid (96 grams) was added dropwise over a 4-hour addition period. The mixture was stirred at room temperature overnight and carefully quenched with 500 ml of water. The organic layer was separated and combined with 3-500 ml ethyl ether extracts of the aqueous layer. The combined organic phases were washed, and dried (MgSO$_4$), and the solvent was removed by evaporation in vacuo to produce an oil. The oil was fractionated and by distillation to provide 8.1 grams of 1,2,2-trichloro-2-vinylcyclopropane.

A 2.8 gram portion of the distilled product was slurried in water at room temperature. Potassium permanganate (7.7 grams) was added and the solution was stirred for 4 hours at room temperature while maintaining a constant pH of 7.0 by the addition of dry ice. The reaction mixture was cooled and filtered. The filtrate was slurried with diethylether while the pH was adjusted to 2.0 with hydrochloric acid. The ether layer was washed with saturated aqueous NaCl, dried over MgSO$_4$ and concentrated to dryness by evaporation in vacuo. The crude product was distilled to give 1,2,2-trichlorocyclopropane carboxylic acid; $^1$H nmr ($\delta$, CDCl$_3$) 2.39(q, 2H), 11.7(s, 1H).

Elemental analysis calculated for C$_4$H$_3$O$_2$Cl$_3$: Theory: C, 25.36; H, 1.60; O, 16.89; Cl, 56.15; Found: C, 25.63; H, 1.77; O, 17.03; Cl, 55.96.

EXAMPLE 2

4'-NITROBENZYL 1,2,2-TRICHLOROCYCLOPROPANE CARBOXYLATE

Potassium carbonate (3.5 grams) was added to a solution of 1,2,2-trichlorocyclopropane carboxylic acid (2.4 grams) in N,N-dimethylacetamide under a nitrogen blanket and stirred at room temperature for approximately 30 minutes. 4-Nitrobenzylbromide (2.7 grams) was dissolved in N,N-dimethylacetamide, and added, dropwise, over a 10 minute period at room temperature. The reaction mixture was stirred overnight and then partitioned between ethyl acetate and water. The organic layer was washed, dried (MgSO$_4$), and concentrated by evaporation of the solvent to give 4'-nitrobenzyl 1,2,2-trichlorocyclopropane carboxylate: $^1$H nmr ($\delta$, CDCl$_3$) 2.36(q, 2H), 5.43(s, 2H), 7.98 (q, 4H).

Elemental Analysis calculated for C$_{11}$H$_{18}$N$_1$O$_4$Cl$_3$: Theory: C, 40.71; H, 2.48; N, 4.32; O, 19.72; Cl, 32.77; Found: C, 40.96; H, 2.47; N, 4.12; O, 19.65; Cl, 32.68.

EXAMPLE 3

N-METHYL-1,2,2-TRICHLOROCYCLOPROPANE CARBOXAMIDE

Thionyl chloride (50 ml) was added to a solution of 1,2,2-trichlorocyclopropane carboxylic acid (47.4 grams) in 300 ml of benzene. The reaction mixture was heated to reflux temperature and stirred for approximately 20 hours. The solvents were evaporated in vacuo to provide the intermediate acid chloride derivative, 1,2,2-trichlorocyclopropane carboxylic acid chloride (43.8 grams).

A solution of the acid chloride derivative (9.4 grams) in 200 ml of benzene was stirred and maintained at a temperature below 35° C. using an ice bath while anhydrous methyl amine was bubbled in until saturation of the reaction mixture was achieved. The mixture was stirred and cooled to 20° C. The reaction mixture was filtered, washed, and concentrated to dryness. The product thus formed was recrystallized using hot water to give N-methyl-1,2,2-trichlorocyclopropane carboxamide (mp 71°-72° C.).

Elemental analysis calculated for C$_5$H$_6$Cl$_3$NO: Theory: C, 29.66; H, 2.99; Cl, 52.53; N, 6.92; Found: C, 29.78; H, 2.91; Cl, 52.80; N, 6.89.

EXAMPLE 4

1,2,2-TRICHLOROCYCLOPROPANE CARBOXYLIC ACID HYDRAZIDE

A solution of 1,2,2-trichlorocyclopropane carboxylic acid chloride (10.4 grams) and ethanol (100 ml) was stirred at reflux temperature for approximately 16 hours. The solvent wws stripped off and the residue was distilled to produce ethyl 1,2,2-trichlorocyclopropane carboxylate.

A solution of ethyl 1,2,2-trichlorocyclopropane carboxylate (3 grams), ethanol (25 ml), and anhydrous hydrazine (0.48 grams) was heated to reflux for approximately 2 hours. The reaction mixture was cooled, the solvent was stripped from solution, and the residue was recrystallized using a small volume of ethanol to produce 1,2,2-trichlorocyclopropane carboxylic acid hydrazide (mp 122°-123° C.). The identity of the final product was confirmed by NMR analysis.

Elemental analysis calculated for C$_4$H$_5$Cl$_3$N$_2$O: Theory: C, 23.61; H, 2.48; Cl, 52.28; N, 13.77; Found: C, 23.73; H, 2.38; Cl, 52.48; N, 13.63.

EXAMPLE 6

METHYL 1,2,2-TRICHLOROCYCLOPROPANE CARBOXYLATE

Potassium carbonate (4.14 grams) and methyl iodide (3.74 ml) were added to a solution of 1,2,2-trichlorocyclopropane carboxylic acid (5.68 grams) and N,N-dimethylacetamide (50 ml). The reaction mixture was stirred for approximately 20 hours and then filtered. Ethyl ether (250 ml) was added to the filtrate and the resultant mixture was washed, dried, and evaporated in vacuo to the desired product, methyl 1,2,2-trichlorocyclopropane carboxylate. Structure of the product was confirmed by NMR.

EXAMPLE 6

ETHYL 1,2,2-TRICHLOROCYCLOPROPANE CARBOXYLATE 1,2,2-trichlorocyclopropane carboxylic acid chloride (10.4 g, 0.05 mole) was added dropwise, with stirring, to 100 ml of 2B ethanol. The reaction mixture was stirred and heated to reflux temperature for about 16 hours. The ethanol was evaporated from the reaction mixture to provide the product as a crude oil which was distilled under reducing pressure to provide 7.2 g of the title product (bp 66°–68° C./2.5 mm).

Analysis calculated for $C_6H_7Cl_3O_2$: Theory: C, 33.14; H, 3.24; Cl, 48.91; Found: C, 33.37; H, 3.18; Cl, 49.02.

EXAMPLE 7

BENZYL 1,2,2-TRICHLOROCYCLOPROPANE CARBOXYLATE

To a stirred solution of 9.47 g (0.05 mole) of 1,2,2-trichlorocyclopropane carboxylic acid in 100 ml of reagent grade acetone was added 6.91 g (0.05 mole) of anhydrous potassium carbonate. To this stirred mixture was added 10.26 g (0.06 mole) of benzyl bromide diluted with a small volume of acetone. The reaction mixture was stirred overnight at room temperature and filtered with suction. The insoluble material was washed on the filter with additional acetone. The acetone wash solutions and the filtrate were combined and evaporated in vacuo to dryness. The resulting product residue was dissolved in 200 ml of diethyl ether and washed twice with water, once with saturated sodium chloride solution and dried over anhydrous magnesium sulfate. Evaporation of the ether solvent provided a straw-colored semi-viscous liquid which distilled at 145°–146° C./3 mm (5.31 g) identified as the title product.

Analysis calculated for $C_{11}H_9Cl_3O_2$: Theory: C, 47.26; H, 3.25; Cl, 38.05; Found: C, 47.55; H, 3.54; Cl, 38.27.

Illustrative of other trihalocyclopropane carboxylic acids and derivatives thereof useful in the method of the present invention are:

1-bromo-2,2 dichlorocyclopropane carboxylic acid;
2,2-dibromo-1-chlorocyclopropane carboxylic acid;
1,2,2-tribromocyclopropane carboxylic acid;
1,2,2-trichlorocyclopropane hydroxamic acid;
1,2,2-trichlorocyclopropane carboxylic acid morpholinamide;
1-bromo-2,2-dichlorocyclopropane carboxylic acid hydrazide;
N-acetyl-1,2,2-trichlorocyclopropane carboxamide;
4'-chlorobenzyl-2,2,2-trichlorocyclopropane carboxylate;
benzhydryl 1-bromo-2,2-dichlorocyclopropane carboxylate;
propyl 1,2,2-tribromocyclopropane carboxylate;
N-phenyl-1,2,2-trichlorocyclopropane carboxamide;
N-methyl-N-butanoyl-2,2-dibromo-1-chlorocyclopropane carboxamide;
N-benzoyl-1-bromo-2,2-dichlorocyclopropane carboxamide;
2,2-dibromo-1-chlorocyclopropane hydroxamic acid;
1,2,2-trichlorocyclopropane carboxylic acid methylhydrazide;
1,2,2-trichlorocyclopropane carboxylic acid phenylhydrazide;
1,2,2-tribromocyclopropane carboxylic acid morpholinamide;
4'-nitrobenzyl-1-bromo-2,2-dibromocyclopropane carboxylate;
4'-chlorobenzyl-1,2,2-tribromocyclopropane carboxylate;
2'-nitrobenzyl-1,2,2-trichlorocyclopropane carboxylate;
N,N-diethyl-1,2,2-trichlorocyclopropane carboxamide;
N-phenyl-N-methyl-1,2,2-trichlorocyclopropane carboxamide;
2'-chlorobenzyl 1-chloro-2,2-dibromocyclopropane carboxylate; and
benzhydryl 1,2,2-trichlorocyclopropane carboxylate.

The compounds defined by the above formula are employed in the regulation of growth of various plant species according to the method of this invention. Typical plant responses embraced by terms such as "plant growth regulation" include inhibition of vegetative growth in herbaceous plants, control of flowering, inhibition of seed formation, control of fruiting, delay in maturation, control of color, and related growth regulatory responses.

The growth regulatory action of the compounds defined above may be advantageously employed in various ways. The production of shorter and thicker stems in plants such as soybeans may reduce the tendency toward lodging resulting in improved harvests and reduced economic loss. Controlling flowering and fruiting in some plant species may be advantageous for hybridization in the production of seedless fruit. Modifying the vegetative process or altering the time and/or degree of flowering and fruiting may result in more advantageous harvest dates as well as increased or modified flower, fruit, or seed production. Useful chemical pruning of trees, shrubs, ornamentals, and nursery stock may also be obtained as well as retardation of plant senescence to prolong field and storage life. Other applications employing compounds defined herein will suggest themselves to those skilled in the art of agriculture and plant growth regulation.

The various plant species whose growth can be regulated according to the method of this invention include bean species such as soybean, and crop species such as corn, wheat, rye, flax, rice, and barley and cotton.

Application of Example 1 to soybeans during the late vegetative through the reproductive phases causes an increase in the number of flowers to be seen at each node as compared to non-treated plants. The flowers are born in a tight cluster with the majority not forming pods. This effect on increased flowers/reduced pods is evident in Tables XII, XVII, and XVIII and suggests that the present compounds can advantageously be employed to treat ornamentals to increase flowering.

The method for regulating the growth of plants provided by this invention comprises applying to the plants an effective amount of a plant growth regulator as defined by the above general formula. The application of active compound can be accomplished by contacting the foliage of the plants with the active compound, or by applying the compound to the soil or habitat in which the plant is growing. The compounds can also be applied directly to seeds.

The specific amount of active plant growth regulator compound to be applied according to the new method will be determined by one or more of several factors, including, the particular plant species being treated, the mode of compound application, the soil texture and moisture content, the particular period of the growing cycle during which the method is practiced, and related factors. Generally, the trihalocyclopropane carboxylic acid plant growth regulators will be applied at an effective rate of about 0.5 to about 2 pounds per acre. Higher application rates, while possible, are not often cost efficient.

For use contemplated according to the method of this invention, the trichlorocyclopropane carboxylic acid growth regulator compounds are formulated into compositions suited to soil, surface, or foliar application to plants and areas where plants are growing. Such compositions can be formulated with any number of well-known and routinely used agronomically acceptable carriers, diluents, excipients, and the like. The compositions may take the form of wettable powders, dusts, granules, solutions, emulsifiable concentrates, emulsions, suspension concentrates, and the like. Such compositions generally contain from about 1 to about 95 percent active ingredient.

A preferred composition for use according to the present method is a wettable powder. Wettable powders generally contain from about 20 to about 80 percent by weight of active ingredient. The remainder of the composition consists of solid carriers and wetting agents. Commonly utilized solid carriers include bentonite, fuller's earth, diatomaceous earth, diatomaceous silica, talc, chalk, hydrated silica, expanded mica, and related carriers. Wetting agents and surfactants commonly employed include condensed aryl sulfonic acids, sodium lignosulfate, condensate blends, alkyl aryl polyether alcohols, anionic and nonionic wetting agents, and the like.

The compounds employed in the method of this invention can be used individually or in a mixture with one or more other active compounds. Such compounds can also be employed in combination with other commonly used agricultural chemicals such as herbicides, fungicides, insecticides, and plant bactericides.

While all of the compounds for use according to the present invention exhibit some regulation of plant growth, certain compounds are more effective than others. Accordingly, preferred compounds of the present invention are those wherein each X is simultaneously chloro, Y=chloro, and R=hydroxy or 4-nitrobenzyloxy. One of the most useful compounds of this preferred group has been shown to be 1,2,2-trichlorocyclopropane carboxylic acid. While it is understood that there are many other useful embodiments of the present invention, plant growth regulant use of the trichlorocyclopropane carboxylic acid is a most preferred embodiment of this invention.

The plant growth regulating activity of the compounds defined above has been demonstrated for representative compounds in standard greenhouse studies. One such test was a broad spectrum plant physiology screen carried out by filling square pots with a sterilized growing soil medium and planting seeds of tomato (*Lycopersicon esculentum*), large crabgrass (*Digitaria sanguinalis*), and redroot pigweed (*Amaranthus retroflexus*).

Pots prepared for postemergence treatment were planted 10 to 13 days prior to treatment and placed in a growth chamber under artificial lighting. Pots for preemergence treatment were planted 1 to 2 days prior to treament. The pots received 12 to 18 hours of light per day and were subject to temperatures of 75° to 85° F.

The test compounds were formulated for application by dissolving a 15 mg sample of each compound in 0.6 ml of a 1:1 mixture of acetone and ethanol containing a small amount of Toximul R and Toximul S surfactants (Toximul R and Toximul S surfactants, manufactured by Stepan Chemical Co., Northfield, Ill., are proprietary blends of anionic and nonionic surface active agents commonly employed in plant growth regulator formulations). The solution was then diluted with deionized water to a final volume of 6.0 ml.

The formulated compounds were evaluated as a soil drench (preemergence application) and as a foliar spray (postemergence application). Preemergence applications were sprayed on the soil one day after the seeds were planted. Postemergence applications were made by spraying the solution over the emerged plants about 12 days after the weeds were planted. The formulated compounds were applied to the planted pots at an effective rate of 15 pounts per acre.

Growth regulating effects of the test compounds were evaluated by two injury rating systems 18 to 21 days after preemergence treatment and 12 to 14 days after postemergence treatment. The degree of plant injury was based on a 1 to 5 scale and a single numerical rating was assigned to each test species as follows:

1 = no injury or effect;
2 = slight injury or effect;
3 = moderate injury or effect;
4 = severe injury or effect;
5 = death of all plants.

The type of injury was also classified and recorded on the test result sheet. One or more of the following types of injury were assigned to each indicator species:

A = Abscission;
B = Burning;
C = Chlorosis;
D = Death;
E = Epinasty;
F = Formative effects;
G = Dark green color;
I = Increased growth;
M = Morphological changes in leaf structure;
N = No emergence;
P = Purple pigmentation;
R = Reduced emergence;
S = Stunting;
Z = Increased branching.

Table I below presents the growth regulating activity of typical trichlorocyclopropane type compounds used according to the method of the present invention in a broad spectrum screen as described above.

TABLE I

| PLANT PHYSIOLOGY SCREEN | | | | |
|---|---|---|---|---|
| Compound | Application Method | Tomato | Crabgrass | Pigweed |
| 1,2,2-trichlorocyclopropane carboxylic acid | Soil Drench | 1 | 3RS | 1 |
| | Foliar Spray | 1 | 4BS | 4BS |
| 1,2,2-trichlorocyclopropane 4-nitrobenzyl carboxylate | Soil Drench | 1 | 2S | 1 |
| | Foliar Spray | 4CS | 4BS | 3S |
| 1,2,2-trichlorocyclopropane methyl carboxylate | Soil Drench | 1 | 1 | 1 |

TABLE I-continued

PLANT PHYSIOLOGY SCREEN

| Compound | Application Method | Tomato | Crabgrass | Pigweed |
|---|---|---|---|---|
| | Foliar Spray | 1 | 1 | 1 |

Similar greenhouse studies were carried out, to further evaluate preemergence (soil drench) and postemergence (foliar spray) growth regulating activities of the trichlorocyclopropane compounds of this invention. The compounds evaluated were formulated according to the procedure outlined above, except that the compounds were applied at the effective rate of 8 lbs/acre.

Eight seed species were utilized. All plantings were made in plastic or galvanized pans (flats). Flats prepared for postemergence treatment were planted 8 to 11 days prior to treatment. Preemergence flats were planted 1 to 2 days prior to treatment. Environmental conditions included a temperature of 75° to 85° F. and a daylength period ranging from 12 to 18 hours. Typical results of such evaluations are presented below in Table II.

TABLE II

| Compound of Example No. | Application Method | Soybean | Barley | Mustard | Large Crabgrass | Morning Glory | Foxtail Millet | Tomato | Redroot Pigweed |
|---|---|---|---|---|---|---|---|---|---|
| 1 | Foliar Spray | — | — | 3FBS | 4BS | 3FBS | 4GFS | 2FS | 3FS |
| 3 | Soil Drench | 1 | 1 | 1 | 1 | 1 | 1 | 1 | 1 |
|   | Foliar Spray | 1 | 1 | 2SF | 1 | 1 | 1 | 2FS | 2S |
| 4 | Soil Drench | 3SFG | 2S | 2SF | 5D | 2S | 4BS | 2FS | 2FS |
|   | Foliar Spray | 2BS | 1 | 2SB | 2SB | 3BS | 3SB | 1 | 3BS |
| 6 | Soil Drench | 2BF | 1 | 1 | 1 | 1 | 1 | 1 | 1 |
|   | Foliar Spray | 1 | 1 | 1 | 1 | 1 | 1 | 1 | 1 |
| 7 | Soil Drench | 3SGZ | 2S | 2FS | 4BS | 2BS | 2BS | 2S | 2SGF |
|   | Foliar Spray | 3BSC | 2BS | 2BS | 4BS | 2B | 4SB | 1 | 2BS |

The growth regulating activity of a number of the more active trichlorocyclopropanes used according to the method of the invention was evaluated at various application rates in a multiple species greenhouse test. The compounds were formulated as described above and applied postemergence to growing plants. The results for certain compounds used according to the method of the present invention are presented below in Tables III and IV.

TABLE III

| Compound of Example No. | Application Rate lbs/A | Soybean | Sugar Beet | Rice | Cotton |
|---|---|---|---|---|---|
| 1 | 1 | 5FGS | 0 | 0 | 2F |
|   | 2 | 7FSG | 0 | 4S | 4FS |
|   | 4 | 7FSG | 5SF | 7S | 7FSB |
| 5 | 4 | 5SF | 0 | 0 | 3FS |

Scale 0-10:
0 = No Effect
10 = Most Severe Effect

TABLE IV

| Compound of Example No. | Application Rate lbs/A | Soybean | Barley | Beet | Rice | Cotton | Wheat |
|---|---|---|---|---|---|---|---|
| 1 | 1 | 3GF | 0 | 0 | 0 | 0 | 0 |
|   | 2 | 4FGS | 3S | 0 | 0 | 2F | 0 |
|   | 4 | 5FGS | 5S | 3F | 5S | 3F | 3S |

Scale 0-10:
0 = No Effect
10 = Most Severe Effect

The results of typical evaluations of several plant growth regulator effects on various plant species are presented in Tables V-VIII. Evaluations of plant growth regulator effects and plant injury were made on a scale of 0 to 3, with 0 indicating no effect and 3 indicating a distinct or severe effect. A "+" sign designates promotion, while a "−" sign designates inhibition or depression. Letter descriptions are the same as set forth above.

TABLE V

Plant Growth Regulator Effect on Height
Application Method: Foliar Spray

| Compound of Example No. | Application Rate lbs/A | Foxtail | Barley | Soybean |
|---|---|---|---|---|
| 1 | 1 | −2 | 0 | −3 |
|   | 2 | −3 | 0 | −3 |
|   | 4 | −3 | 0 | −3 |
| 2 | 1 | −2 | −1 | −2 |
|   | 2 | −3 | −1 | −3 |
|   | 4 | −3 | −2 | −3 |

TABLE VI

Plant Growth Regulator Effect on Branching and Injury
Application Method: Foliar Spray

| Compound of Example No. | Application Rate lbs/A | Soybeans Branching | Soybeans Injury |
|---|---|---|---|
| 1 | 1 | +2 | +2M |
|   | 2 | +1 | +2MB |
|   | 4 | +2 | +3MB |
| 2 | 1 | +1 | +2M |
|   | 2 | +1 | +2M |
|   | 4 | +2 | +2M |

TABLE VII

Plant Growth Regulator Effects on Seedhead Formation
Application Method: Foliar Spray

| Compound of Example No. | Application Rate lbs/A | Foxtail |
|---|---|---|
| 1 | 4 | −1 |
| 2 | 4 | −2 |

TABLE VIII

Plant Growth Regulator Effect on Tillering
Application Method: Foliar Spray

| Compound of Example No. | Application Rate lbs/A | Barley |
|---|---|---|
| 2 | 1 | +1 |
|   | 2 | +1 |
|   | 4 | +1 |

Two of the preferred compounds used according to the method of the present invention have been further evaluated in a number of greenhouse studies to determine their plant growth regulating effects on soybeans. In a typical test, the compounds were applied postemergence as a foliar spray. The studies involved randomized blocks with three replicates. Observations were made for average plant height, axillary branch length, and pod weight and growth.

The results of the greenhouse tests for 1,2,2-trichlorocyclopropane carboxylic acid (50% wettable powder) and 1,2,2-trichlorocyclopropane 4-nitrobenzyl carboxylate are presented below in Tables IX-XII. The data presented compares treated soybeans to untreated soybeans, the untreated controls being assigned a rating of 100 percent.

TABLE IX

Plant Growth Regulator Effect on Length of Terminal Axillary Branch

| Compound of Example No. | Application Rate lb/A | Length (cm) 1 | 2 | 3 | Man Length (cm) | Percent of Control |
|---|---|---|---|---|---|---|
| 1 | 0.5 | 27.00 | 23.00 | 26.00 | 25.33 | 71.4 |
|   | 1.0 | 17.00 | 14.00 | 4.00 | 11.67 | 32.9 |
|   | 2.0 | 14.00 | 17.00 | 18.00 | 16.33 | 46.0 |
| 2 | 0.5 | 29.00 | 42.00 | 24.00 | 31.67 | 89.2 |
|   | 1.0 | 30.00 | 11.00 | 30.00 | 23.67 | 66.7 |
|   | 2.0 | 24.00 | 12.00 | 17.00 | 17.67 | 49.8 |
| Control | 0 | 41.00 | 26.00 | 34.00 | 35.50 | 100.0 |

TABLE X

Plant Growth Regulator Effect on Length of Basal Axillary Branch

| Compound of Example No. | Application Rate lb/A | Length (cm) 1 | 2 | 3 | Mean Length (cm) | Percent of Control |
|---|---|---|---|---|---|---|
| 1 | 0.5 | 14.00 | 20.00 | 12.00 | 15.33 | 49.2 |
|   | 1.0 | 18.00 | 14.00 | 4.00 | 12.00 | 38.5 |
|   | 2.0 | 3.00 | 6.00 | 9.00 | 6.00 | 19.3 |
| 2 | 0.5 | 46.00 | 35.00 | 36.00 | 39.00 | 125.1 |
|   | 1.0 | 39.00 | 12.00 | 36.00 | 29.00 | 93.0 |
|   | 2.0 | 20.00 | 18.00 | 12.00 | 16.67 | 53.5 |
| Control | 0 | 30.00 | 27.00 | 36.00 | 31.17 | 100.0 |

TABLE XI

Plant Growth Regulator Effect on Weight of Pods in Grams

| Compound of Example No. | Application Rate lb/A | Weight of Pods (gm) 1 | 2 | 3 | Mean Weight (gm) | Percent of Control |
|---|---|---|---|---|---|---|
| 1 | 0.5 | 7.30 | 5.40 | 2.70 | 5.13 | 68.1 |
|   | 1.0 | 1.60 | 0.00 | 0.00 | 0.53 | 7.1 |
|   | 2.0 | 0.00 | 0.00 | 0.00 | 0.00 | 0.0 |
| 2 | 0.5 | 9.30 | 10.10 | 4.10 | 7.83 | 104.0 |
|   | 1.0 | 5.60 | 0.95 | 8.60 | 5.05 | 67.0 |
|   | 2.0 | 3.90 | 0.00 | 0.84 | 1.58 | 21.0 |
| Control | 0 | 8.20 | 6.40 | 5.50 | 7.53 | 100.0 |

TABLE XII

Plant Growth Regulator Effect on Number of Pods Per Plant

| Compound of Example No. | Application Rate lb/A | Number of Pods/Plant 1 | 2 | 3 | Mean No. | Percent of Control |
|---|---|---|---|---|---|---|
| 1 | 0.5 | 16.00 | 8.00 | 9.00 | 11.00 | 71.0 |
|   | 1.0 | 3.00 | 0.00 | 0.00 | 1.00 | 6.4 |
|   | 2.0 | 0.00 | 0.00 | 0.00 | 0.00 | 0.0 |
| 2 | 0.5 | 22.00 | 17.00 | 10.00 | 16.33 | 105.4 |
|   | 1.0 | 12.00 | 5.00 | 17.00 | 11.33 | 73.1 |
|   | 2.0 | 10.00 | 0.00 | 3.00 | 4.33 | 27.9 |
| Control | 0 | 17.00 | 11.00 | 12.00 | 15.50 | 100.0 |

Additional greenhouse studies were carried out utilizing a 50% wettable powder formulation of 1,2,2-trichlorocyclopropane carboxylic acid. Varying methods of compound application were used, such as an aqueous foliar spray, pre-plant incorporation, soil application following planting, and soil drench. Treated and untreated plots were individually seeded to soybeans. Observations were made 42 days after treatment. Treated plots were compared with untreated controls to determine growth inhibition, percent of crop injury, and pod growth. Tables XIII-XVIII present the growth regulatory effects of these various application methods on soybean growth.

TABLE XIII

Plant Growth Regulator Effect on Average Plant Height in Cms.

| Application Rate (lb/A) | Application Method | Average Plant Height (cms) 1 | 2 | 3 | Mean Plant Height (cm) | Percent of Control |
|---|---|---|---|---|---|---|
| 1 | Pre-plant Incorporated | 34.00 | 20.60 | 26.00 | 26.87 | 46.4 |
| 2 |  | 19.00 | 21.00 | 38.50 | 26.17 | 45.1 |
| 1 | Soil Application | 29.00 | 35.50 | 20.00 | 28.17 | 48.6 |
| 2 |  | 13.60 | 30.50 | 24.50 | 22.87 | 39.5 |
| 1 | Foliar Application | 43.00 | 48.00 | 49.00 | 46.67 | 80.5 |
| 2 |  | 38.00 | 50.00 | 42.00 | 43.33 | 74.8 |
| 1 | Soil Drench | 47.00 | 37.00 | 45.00 | 43.00 | 74.2 |
| 2 |  | 43.00 | 48.00 | 41.00 | 44.00 | 75.9 |
| Control |  | 50.00 | 59.00 | 57.00 | 57.94 | 100.0 |

*0-10 Scale

TABLE XIV

Plant Growth Regulator Effect on Weight of Two Plants in Grams

| Application Rate (lb/A) | Application Method | Average Weight of Two Plants in Grams 1 | 2 | 3 | Mean Weight of Two Plants (cm) | Percent of Control |
|---|---|---|---|---|---|---|
| 1 | Pre Plant Incorporated | 29.50 | 19.30 | 22.40 | 23.73 | 58.7 |
| 2 |  | 12.60 | 9.60 | 23.00 | 15.07 | 37.3 |
| 1 | Soil Application | 24.00 | 25.20 | 16.20 | 21.80 | 53.9 |

TABLE XIV-continued

Plant Growth Regulator Effect on Weight of Two Plants in Grams

| Application Rate (lb/A) | Application Method | Average Weight of Two Plants in Grams | | | Mean Weight of Two Plants (cm) | Percent of Control |
|---|---|---|---|---|---|---|
| | | 1 | 2 | 3 | | |
| 2 | | 14.00 | 19.50 | 15.70 | 16.40 | 40.6 |
| 1 | Foliar Application | 38.20 | 36.00 | 37.20 | 37.13 | 91.9 |
| 2 | | 26.40 | 39.70 | 31.80 | 32.63 | 80.8 |
| 1 | Soil Drench | 35.20 | 30.60 | 34.50 | 33.43 | 82.7 |
| 2 | | 39.10 | 40.10 | 30.60 | 36.60 | 90.6 |
| Control | | 39.20 | 42.70 | 37.10 | 40.41 | 100.0 |

TABLE XV

Plant Growth Regulator Effect on Crop Injury Rating

| Application Rate (lb/A) | Application Method | Crop Injury Rating* | | | Mean Crop Injury Rating | Percent of Control |
|---|---|---|---|---|---|---|
| | | 1 | 2 | 3 | | |
| 1 | Pre-plant Incorporated | 8.00 | 8.00 | 9.00 | 8.33 | 83.3 |
| 2 | | 10.00 | 10.00 | 8.00 | 9.33 | 93.3 |
| 1 | Soil Application | 8.00 | 7.00 | 10.00 | 8.33 | 83.3 |
| 2 | | 10.00 | 8.00 | 8.00 | 8.67 | 86.7 |
| 1 | Foliar Application | 3.00 | 2.00 | 4.00 | 3.00 | 30.0 |
| 2 | | 3.00 | 3.00 | 3.00 | 3.00 | 30.0 |
| 1 | Soil Drench | 4.00 | 4.00 | 3.00 | 3.67 | 36.7 |
| 2 | | 4.00 | 3.00 | 3.00 | 3.33 | 33.3 |
| Control | | 0.00 | 0.00 | 0.00 | 0.00 | 00.0 |

*Crop Injury Rating Scale:
0 = None
1-3 = Slight
4-6 = Moderate
7-9 = Severe

TABLE XVI

Plant Growth Regulator Effect on Crop Color

| Application Rate (lb/A) | Application Method | Crop Color Rating 0-10 Scale* | | | Mean Crop Color Rating | Percent of Control |
|---|---|---|---|---|---|---|
| | | 1 | 2 | 3 | | |
| 1 | Pre-plant Incorporated | 4.00 | 5.00 | 8.00 | 5.67 | 56.7 |
| 2 | | 8.00 | 8.00 | 5.00 | 7.00 | 70.0 |
| 1 | Soil Application | 5.00 | 6.00 | 8.00 | 6.33 | 63.3 |
| 2 | | 8.00 | 8.00 | 8.00 | 8.00 | 80.0 |
| 1 | Foliar Application | 1.00 | 1.00 | 1.00 | 1.00 | 10.0 |
| 2 | | 4.00 | 3.00 | 2.00 | 3.00 | 30.0 |
| 1 | Soil Drench | 3.00 | 4.00 | 3.00 | 3.33 | 33.3 |
| 2 | | 3.00 | 3.00 | 2.00 | 2.67 | 26.7 |
| Control | | 0.00 | 0.00 | 0.00 | 0.00 | 0.00 |

*Crop Injury Rating Scale:
0 = None
1-3 = Slight
4-6 = Moderate
7-9 = Severe

TABLE XVII

Plant Growth Regulator Effect on Number of Pods of Two Plants

| Application Rate (lb/A) | Application Method | Average Number of Pods of Two Plants | | | Mean Number of Pods | Percent of Control |
|---|---|---|---|---|---|---|
| | | 1 | 2 | 3 | | |
| 1 | Pre-plant Incorporated | 5.00 | 0.00 | 6.00 | 3.67 | 20.4 |
| 2 | | 0.00 | 0.00 | 2.00 | 0.67 | 3.7 |
| 1 | Soil Application | 1.00 | 0.00 | 0.00 | 0.33 | 1.8 |
| 2 | | 0.00 | 0.00 | 0.00 | 0.00 | 0.0 |
| 1 | Foliar Application | 3.00 | 0.00 | 5.00 | 2.67 | 14.8 |
| 2 | | 0.00 | 0.00 | 0.00 | 0.00 | 0.0 |
| 1 | Soil Drench | 0.00 | 0.00 | 0.00 | 0.00 | 0.0 |
| 2 | | 0.00 | 0.00 | 0.00 | 0.00 | 0.0 |
| Control | | 20.00 | 21.00 | 18.00 | 18.00 | 100.0 |

TABLE XVIII

Plant Growth Regulator Effect on Total Weight of Pods of Two Plants

| Application Rate (lb/A) | Application Method | Average Total Weight of Pods of Two Plants (grams) | | | Mean Total Weight of Pods of Two Plants (grams) | Percent of Control |
|---|---|---|---|---|---|---|
| | | 1 | 2 | 3 | | |
| 1 | Pre-plant Incorporated | 1.20 | 0.00 | 1.70 | 0.97 | 11.6 |
| 2 | | 0.00 | 0.00 | 0.50 | 0.17 | 2.0 |
| 1 | Soil Application | 0.20 | 0.00 | 0.00 | 0.07 | 0.8 |
| 2 | | 0.00 | 0.00 | 0.00 | 0.00 | 0.0 |
| 1 | Foliar Application | 1.00 | 0.00 | 2.00 | 1.00 | 12.0 |
| 2 | | 0.00 | 0.00 | 0.00 | 0.00 | 0.0 |
| 1 | Soil Drench | 0.00 | 0.00 | 0.00 | 0.00 | 0.0 |
| 2 | | 0.00 | 0.00 | 0.00 | 0.00 | 0.0 |
| Control | | 10.20 | 9.10 | 7.30 | 8.30 | 100.0 |

The growth regulating activity of 1,2,2-trichlorocyclopropane carboxylic acid was also evaluated with respect to cotton plant applications at varying stages of growth. Standard greenhouse tests, conducted as described above for soybeans, are summarized below in Tables XIX and XX. The compound was foliar applied at the beginning of flowering, mature boll, or at the vegetative growth stage. Observations were made of crop color, crop injury, leaf morphology, and boll production by comparing treated plants to untreated plants (the controls). A dash in Table XIX indicates no evaluation was made. In order to assess a crop color rating, the control plant was assigned the number 100. A number greater than 100 indicates a color that is darker than that of the control plant. Crop injury was evaluated on a scale of 0-100, where 0=no injury; 10-30=slight; 40-60=moderate; 70-90=severe; and 100=death. Injury resulting from treatment at the time of flowering was characterized as necrotic spots. Application at boll stages resulted in fruit shed. Leaf morphology was also evaluated on a scale of 0-100. Application at the time of flowering resulted in cupping of leaves. Boll stage applications resulted in cupping and thickening of leaves.

bean plants at various stages of vegetative and reproductive development.

The descriptions of the various soybean vegetative and reproductive stages are summarized below.

| Abbreviated Stage Title | Description |
|---|---|
| DESCRIPTION OF SOYBEAN VEGETATIVE STAGES | |
| Emergence | Cotyledons above the soil surface. |
| Cotyledon | Unifoliolate leaves unrolled sufficiently so the leaf edges are not touching. |
| First-node | Fully developed leaves at unifoliolate nodes. |
| Second-node | Fully developed trifoliolate leaf at node above the unifoliolate nodes. |
| Fourth-node | Four nodes on the main stem with fully developed leaves beginning with the unifoliolate nodes. |
| nth-node | n number of nodes on the main stem with fully developed leaves beginning with the unifoliolate nodes. n can be any number beginning with 1 for first-node stage. |
| DESCRIPTION OF REPRODUCTIVE STAGES | |
| Beginning bloom | One open flower at any node on the main stem. |
| Full bloom | Open flower at one of the two uppermost nodes on the main stem with a fully developed leaf. |
| Beginning pod | Pod 5 mm long at one of the four uppermost nodes on the main stem with a fully developed leaf. |
| Full pod | Pod 2 cm long at one of the four uppermost nodes on the main stem with a fully developed leaf. |
| Beginning seed | Seed 3 mm long in a pod at one of the four uppermost nodes on the main stem with a fully developed leaf. |
| Full seed | Pod containing a green seed that fills the pod cavity at one of the four uppermost nodes on the main stem with a fully developed leaf. |
| Beginning maturity | One normal pod on the main stem that has reached its mature pod color. |
| Full maturity | Ninety-five percent of the pods that have reached their mature pod color. Five to ten days of drying weather |

TABLE XIX

Plant Growth Regulating Effect on Cotton at Flowering and Boll Growth Stages

| Application Rate lb/A | Time of Application | Crop Color | | Crop Injury | | | Leaf Morphology | | | Number of Bolls Per Plant |
|---|---|---|---|---|---|---|---|---|---|---|
| | | (Mid) | (Late) | (Early) | (Mid) | (Late) | (Early) | (Mid) | (Late) | |
| 1.0 | Flowering Stage | 100 | 100 | 10 | 0 | 30 | 5 | 5 | 0 | 65 |
| 2.0 | Flowering Stage | 105 | 110 | 13 | 7 | 47 | 10 | 15 | 17 | 59 |
| 1.0 | Boll Growth Stage | 101 | 103 | — | 5 | 23 | — | 12 | 20 | 62 |
| 2.0 | Boll Growth Stage | 100 | 107 | — | 28 | 50 | — | 27 | 23 | 33 |
| 0 (Control) | Boll Growth Stage | 100 | 100 | 0 | 0 | 0 | 0 | 0 | 0 | 100 |

TABLE XX

Plant Growth Regulating Effect on Cotton at Vegetative Growth Stage

| Application Rate lb/A | Percent of Control | | | |
|---|---|---|---|---|
| | Growth in cm | Squares/Plant | Crop Color | Leaf Morphology |
| 0.25 | 102 | 102 | 0 | 0 |
| 0.5 | 98 | 108 | 0 | 7 |
| 1.0 | 92 | 113 | 0 | 3 |
| 2.0 | 97 | 113 | 0 | 20 |
| Control | 100 | 100 | 0 | 0 |

Soybean Field Test

Further plant field trial tests were completed for 1,2,2-trichlorocyclopropane carboxylic acid to determine its growth regulating effects when applied to soy-

| Abbreviated Stage Title | Description |
|---|---|
| | are required before the soybeans have less than 15 percent moisture. |

The compound of Example 1 was tested on soybeans growing in field plots in the Midwestern United States. Williams 82 soybeans were planted in 38 inch rows at a population of 55 lb of seed per acre. The compound of Example 1 was formulated as a 50 weight percent wettable powder. Each treatment rate was applied to 4 replicates; each replicate consisted of 2 rows, 25 feet in length. Three application times were used, at the fifth trifoliolate, at the beginning of flowering, and at the full pod growth stage.

The compound formulations were applied to the foliage of the soybean plants in a volume of 50 gallons per acre, using two hollow cone spray tips per row. A nonionic surfactant was added to the final spray compositions at a concentration of 0.1% by volume.

The vegetative stage applications were made July 13, 1984, the flowering stage applications were made July 23, 1984, and the full pod applications were made on Aug. 13, 1984. On Sept. 1, 1984, the plants were rated by skilled observers and morphology ratings were assigned, on a scale where 1-3 indicate slight effects, 4-6 indicate moderate effects, and 7-9 indicate severe effects. In some cases, a morphology rating was also completed in mid-August. The row height and canopy width were also measured, and are reported as a percentage of the measurements of the control rows.

On Oct. 10, 1984, further observations were made and plant lodging and crop senescence were rated. Lodging was rated on a 0-5 scale with 5 indicating complete lodging of the crop. Senescence was evaluated on a scale by which 100 indicates completely senesced plants and 200 indicates completely green plants.

On Oct. 31, 1984, when the soybeans were mature, they were harvested and the yield was calculated as a percentage of the yield of untreated control plots.

The observed results of the tests are set forth in Tables XXI-XXIII.

TABLE XXI

| Rate lb/A | Vegetative Application | | | | | | |
|---|---|---|---|---|---|---|---|
| | Morphology | | Height | Width | Lodging | Senescence | Yield |
| | Aug. | Sept. | | | | | |
| 0.125 | 1.3 | 1.8 | 103 | 100 | 2.0 | 101 | 101 |
| 0.25 | 3.3 | 4.5 | 99 | 99 | 2.0 | 104 | 99 |
| 0.5 | 5.3 | 7.0 | 101 | 86 | 1.6 | 110 | 86 |
| 1.0 | 6.3 | 7.5 | 99 | 78 | 0.8 | 121 | 79 |
| 2.0 | 7.8 | 7.0 | 77 | 61 | 0.4 | 143 | 50 |
| Control | 0 | 0 | 100 | 100 | 2.1 | 100 | 100 |

TABLE XXII

| Rate lb/A | Flowering Application | | | | | | |
|---|---|---|---|---|---|---|---|
| | Morphology | | Height | Width | Lodging | Senescence | Yield |
| | Aug. | Sept. | | | | | |
| 0.125 | 1.3 | 1.5 | 101 | 96 | 1.8 | 100 | 101 |
| 0.25 | 2.5 | 4.0 | 110 | 100 | 1.5 | 103 | 101 |
| 0.5 | 5.8 | 7.8 | 107 | 97 | 1.3 | 110 | 94 |
| 1.0 | 7.0 | 8.5 | 95 | 67 | 0 | 123 | 80 |
| 2.0 | 6.5 | 6.3 | 91 | 71 | 0 | 155 | 54 |
| Control | 0 | 0 | 100 | 100 | 2.1 | 100 | 100 |

TABLE XXIII

| Rate lb/A | Full Pod Application | | | | | | |
|---|---|---|---|---|---|---|---|
| | Morphology | | Height | Width | Lodging | Senescence | Yield |
| | Aug. | Sept. | | | | | |
| 0.125 | — | 0 | 99 | 100 | 2.4 | 103 | 98 |
| 0.25 | — | 0.3 | 107 | 100 | 1.5 | 103 | 102 |
| 0.5 | — | 0 | 106 | 100 | 1.5 | 108 | 98 |
| 1.0 | — | 0.8 | 106 | 95 | 0.9 | 163 | 73 |
| 2.0 | — | 1.0 | 106 | 91 | — | — | — |
| Control | 0 | 0 | 100 | 100 | 2.1 | 100 | 100 |

While we have described the invention with respect to specific materials and procedures, it is to be understood that such matters are illustrative only and not limiting. Numerous modifications and equivalents will be apparent to those of ordinary skill in this art without departing from the spirit of the invention.

We claim:

1. A method for regulating plant growth comprising applying to a plant, in an amount effective to provide growth regulation, a compound of the formula

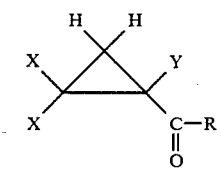

wherein each X is simultaneously chloro or bromo; Y is chloro or bromo; and R represents hydroxy, $C_1$-$C_4$ alkoxy, benzyloxy, nitrobenzyloxy, chlorobenzyloxy, benzhydryloxy, or a group of the formula —$NR_1R_2$ wherein $R_1$ is hydrogen, $C_1$-$C_4$ alkyl or phenyl, and $R_2$ is hydroxy, $C_1$-$C_4$ alkyl, $C_1$-$C_4$ alkanoyl, benzoyl, or a group of the formula —$NHR_3$ wherein $R_3$ is hydrogen, $C_1$-$C_4$ alkyl, phenyl, $C_1$-$C_4$ alkanoyl, or benzoyl;

or $R_1$ and $R_2$, together with the nitrogen atom to which they are attached, form a morpholino group; with the limitation that when $R_1$ is hydrogen, $R_2$ is hydroxy, $C_1$-$C_4$ alkyl, $C_1$-$C_4$ alkanoyl, benzoyl, or a group of the formula —$NHR_3$ wherein $R_3$ is hydrogen, $C_1$-$C_4$ alkyl, phenyl, $C_1$-$C_4$ alkanoyl or benzoyl;

and subject to the further limitation that when $R_1$ is $C_1$-$C_4$ alkyl or phenyl, $R_2$ is $C_1$-$C_4$ alkyl.

2. The method of claim 1 applying a compound wherein X is bromo.

3. The method of claim 1 applying a compound wherein X is chloro.

4. The method of claim 3 applying a compound wherein Y is chloro.

5. The method of claim 4 applying a compound wherein R is a group of the formula —$NR_1R_2$.

6. The method of claim 5 applying a compound wherein R is hydroxyamino.

7. The method of claim 4 applying a compound wherein R is selected from hydroxy or 4-nitrobenzyloxy.

8. The method of claim 7 applying a compound wherein R is hydroxy.

9. The method according to claim 7 wherein the plant is soybeans or cotton.

10. The method of claim 8 wherein the plant is soybeans.

11. A method for enhancing plant flowering comprising applying to a plant, in an amount effective to enhance plant flowering, a compound of the formula

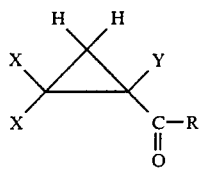

wherein each X is simultaneously chloro or bromo; Y is chloro or bromo; and R represents hydroxy, $C_1$-$C_4$ alkoxy, benzyloxy, nitrobenzyloxy, chlorobenzyloxy, benzhydryloxy, or a group of the formula —$NR_1R_2$ wherein $R_1$ is hydrogen, $C_1$-$C_4$ alkyl or phenyl, and $R_2$ is hydroxy, $C_1$-$C_4$ alkyl, $C_1$-$C_4$ alkanoyl, benzoyl, or a group of the formula —$NHR_3$ wherein $R_3$ is hydrogen, $C_1$-$C_4$ alkyl, phenyl, $C_1$-$C_4$ alkanoyl, or benzoyl;

or $R_1$ and $R_2$, together with the nitrogen atom to which they are attached, form a morpholino group;

with the limitation that when $R_1$ is hydrogen, $R_2$ is hydroxy, $C_1$-$C_4$ alkyl, $C_1$-$C_4$ alkanoyl, benzoyl, or a group of the formula —$NHR_3$ wherein $R_3$ is hydrogen, $C_1$-$C_4$ alkyl, phenyl, $C_1$-$C_4$ alkanoyl or benzoyl;

and subject to the further limitation that when $R_1$ is $C_1$-$C_4$ alkyl or phenyl, $R_2$ is $C_1$-$C_4$ alkyl.

12. The method of claim 11 applying a compound wherein X is bromo.

13. The method of claim 11 applying a compound wherein X is chloro.

14. The method of claim 13 applying a compound wherein Y is chloro.

15. The method of claim 14 applying a compound wherein R is a group of the formula —$NR_1R_2$.

16. The method of claim 15 applying a compound wherein R is hydoxyamino.

17. The method of claim 14 applying a compound wherein R is 4-nitrobenzyloxy.

18. The method of claim 17 applying a compound wherein R is hydroxy.

19. A compound of the formula

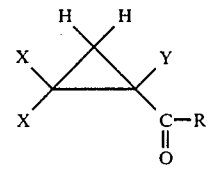

wherein X is chloro; Y is chloro; and R represents benzyloxy, nitrobenzyloxy, chlorobenzyloxy, benzhydryloxy, or a group of the formula —$NR_1R_2$ wherein $R_1$ is hydrogen, $C_1$-$C_4$ alkyl or phenyl, and $R_2$ is hydroxy, $C_1$-$C_4$ alkyl, $C_1$-$C_4$ alkanoyl, benzoyl, or a group of the formula —$NHR_3$ wherein $R_3$ is hydrogen, $C_1$-$C_4$ alkyl, phenyl, $C_1$-$C_4$ alkanoyl, or benzoyl;

or $R_1$ and $R_2$, together with the nitrogen atom to which they are attached, form a morpholino group;

with the limitation that when $R_1$ is hydrogen, $R_2$ is hydroxy, $C_1$-$C_4$ alkyl, or $C_1$-$C_4$ alkanoyl, benzoyl, or a group of the formula —$NHR_3$ wherein $R_3$ is hydrogen, $C_1$-$C_4$ alkyl, phenyl, $C_1$-$C_4$ alkanoyl or benzoyl;

and subject to the further limitation that when $R_1$ is $C_1$-$C_4$ alkyl or phenyl, $R_2$ is $C_1$-$C_4$ alkyl.

20. The compound of claim 19 wherein X is chloro, Y is chloro, and R is 4-nitrobenzyloxy.

21. The compound of claim 19 wherein X is chloro, Y is chloro, and R is benzyloxy.

22. The compound of claim 19 wherein X is chloro, Y is chloro, $R_1$ is hydrogen, and $R_2$ is methyl.

23. The compound of claim 19 wherein X is chloro, Y is chloro, $R_1$ is hydrogen, and $R_2$ is a group of the formula —$NHR_3$ wherein $R_3$ is hydrogen.

* * * * *

UNITED STATES PATENT AND TRADEMARK OFFICE
CERTIFICATE OF CORRECTION

PATENT NO. : 4,704,156
DATED : November 3, 1987
INVENTOR(S) : Lawrence J. McShane It is certified that error appears in the above-identified patent and that said Letters Patent is hereby corrected as shown below:

In column 1, line 32, please delete "known", and insert -- unknown -- therefor.

Column 1, line 60, delete "$c_1-C_4$" and insert -- $C_1-C_4$ -- therefor.

Column 2, line 41, and line 59, please delete "in situ" and insert -- *in situ* -- therefor.

Column 4, line 37, please delete "wws" and insert -- was -- therefor.

Column 4, line 54, please delete "EXAMPLE 6" and insert -- EXAMPLE 5 -- therefor.

Column 8, line 25, please delete "weeds" and insert -- seeds -- therefor.

Column 18, line 48, please delete "$C_{1-C4}$ alkan-" and insert -- $C_1-C_4$ alkan- -- therefor.

Signed and Sealed this

Twelfth Day of July, 1988

Attest:

DONALD J. QUIGG

Attesting Officer

Commissioner of Patents and Trademarks